(12) United States Patent
Kohlstruk et al.

(10) Patent No.: US 9,937,483 B2
(45) Date of Patent: Apr. 10, 2018

(54) PROCESS FOR PREPARING 3-AMINOMETHYL-3,5,5-TRIMETHYLCYCLOHEXYLAMINE

(71) Applicant: Evonik Degussa GmbH, Essen (DE)

(72) Inventors: Stephan Kohlstruk, Gladbeck (DE); Anne Rittsteiger, Olfen (DE); Alexander Martin Ruefer, Recklinghausen (DE); Norbert Schlueter, Gescher (DE); Sven Schneider, Datteln (DE); Sabrina Sowka, Duelmen (DE); Guido Streukens, Wuppertal (DE); Stefan Roeder, Sinntal (DE); Monika Berweiler, Maintal (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 15/082,752

(22) Filed: Mar. 28, 2016

(65) Prior Publication Data

US 2016/0289164 A1 Oct. 6, 2016

(30) Foreign Application Priority Data

Mar. 30, 2015 (EP) .................................... 15161579

(51) Int. Cl.
*C07C 209/48* (2006.01)
*B01J 23/00* (2006.01)
(Continued)

(52) U.S. Cl.
CPC ........... *B01J 23/002* (2013.01); *B01J 23/755* (2013.01); *B01J 23/864* (2013.01); *B01J 23/866* (2013.01);
(Continued)

(58) Field of Classification Search
None
See application file for complete search history.

(56) References Cited

U.S. PATENT DOCUMENTS

2002/0137970 A1  9/2002 Ostgard et al.
2010/0041921 A1  2/2010 Lettmann et al.

FOREIGN PATENT DOCUMENTS

EP  1 216 985 A2  6/2002
EP  1 216 985 A3  6/2002
(Continued)

OTHER PUBLICATIONS

U.S. Appl. No. 09/985,179, filed Nov. 1, 2001, 2002-0087036, Thomas Haas, et al.
(Continued)

*Primary Examiner* — Sudhakar Katakam
*Assistant Examiner* — Jennifer C Sawyer
(74) *Attorney, Agent, or Firm* — Grüneberg and Myers PLLC

(57) ABSTRACT

Isophoronediamine, is prepared by A) subjecting isophoronenitrile directly in one stage to aminating hydrogenation to give isophoronediamine in the presence of ammonia, hydrogen, a hydrogenation catalyst and an optional additive, and in the presence or absence of an organic solvent; or B) first converting isophoronenitrile fully or partly in at least two or more than two stages to isophoronenitrile imine, and subjecting the isophoronenitrile imine to aminating hydrogenation to give isophoronediamine as a pure substance or in a mixture with another component and/or isophoronenitrile, in the presence of at least ammonia, hydrogen and a catalyst.

23 Claims, 1 Drawing Sheet

(51) Int. Cl.

| | | |
|---|---|---|
| | *B01J 23/86* | (2006.01) |
| | *B01J 35/02* | (2006.01) |
| | *B01J 25/00* | (2006.01) |
| | *B01J 35/08* | (2006.01) |
| | *C07C 209/52* | (2006.01) |
| | *C07C 253/30* | (2006.01) |
| | *B01J 23/755* | (2006.01) |
| | *B01J 37/00* | (2006.01) |

(52) U.S. Cl.
CPC ............. *B01J 25/00* (2013.01); *B01J 35/023* (2013.01); *B01J 35/026* (2013.01); *B01J 35/08* (2013.01); *B01J 37/0018* (2013.01); *C07C 209/48* (2013.01); *C07C 209/52* (2013.01); *C07C 253/30* (2013.01); *B01J 2523/00* (2013.01); *C07C 2601/14* (2017.05)

(56) References Cited

FOREIGN PATENT DOCUMENTS

| WO | WO 02/051791 A2 | 7/2002 |
| WO | WO 2008/107226 A1 | 9/2008 |

OTHER PUBLICATIONS

U.S. Pat. No. 6,649,799, Nov. 18, 2003, 2002-0173676, Monika Berweiler, et al.
U.S. Appl. No. 12/278,795, filed Nov. 29, 2006, 2009/0048466, Christian Lettmann, et al.
U.S. Pat. No. 8,877,976, Nov. 4, 2014, 2013/0261341, Christian Lettmann, et al.
U.S. Pat. No. 9,085,506, Jul. 21, 2015, 2013/0253226, Markus Galle, et al.
Extended European Search Report dated Oct. 9, 2015 in Patent Application No. 15161579.6 (with English translation of Categories of Cited Documents).

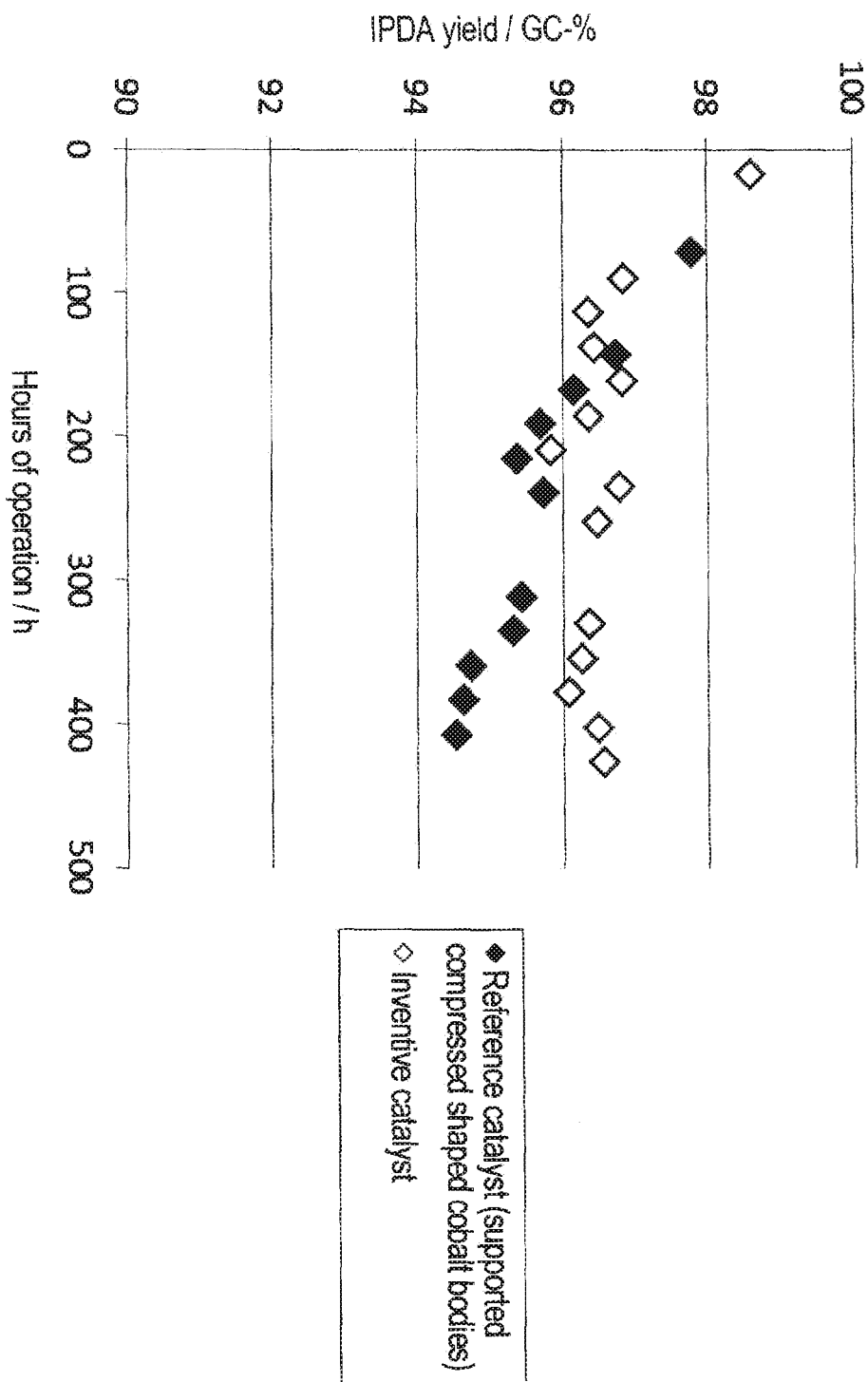

PROCESS FOR PREPARING 3-AMINOMETHYL-3,5,5-TRIMETHYLCYCLOHEXYLAMINE

BACKGROUND OF THE INVENTION

Field of the Invention

The invention relates to an improved process for preparing 3-aminomethyl-3,5,5-trimethylcyclohexylamine, called isophoronediamine or IPDA for short hereinafter, by means of catalytic hydrogenation and/or catalytic reductive amination also referred to as aminating hydrogenation) of 3-cyano-3,5,5-trimethylcyclohexanone, called isophoronenitrile or IPN for short hereinafter.

Discussion of the Background

The preparation of IPDA by aminating hydrogenation of I9N is known and has already been described many times.

In the simplest case (U.S. Pat. No. 3,352,913), IPN is reacted in the presence of hydrogen and of an excess of ammonia over a cobalt catalyst. First of all, IPN and ammonia eliminate water to form isophoronenitrile imine, IPNI, which is subsequently hydrogenated to IPDA.

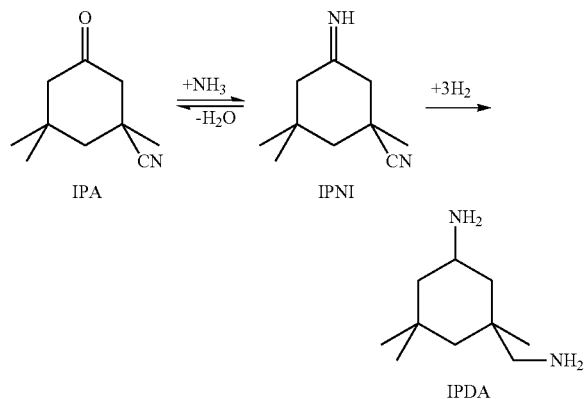

When the reaction is conducted in this way, the yield of IPDA is determined to a crucial degree by the excess of ammonia. The maximum IPDA yields achieved are about 80%. The main by-product is what is called the amino alcohol, IPAA, which results from the direct hydrogenation of the IPN.

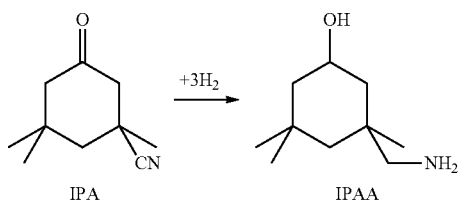

A significant rise in the IPDA yield is achieved when the formation of IPNI is accelerated by use of suitable imination catalysts. Suitable imination catalysts are, for example, acidic ion exchange resins (EP 042 119). In addition, it is also possible to use acidic metal oxides (EP 449 089), sulpho-containing organopolysiloxanes (EP 816 323), heteropolyacids (DE 44 26 472) and activated carbon (EP 061 137) as imination catalysts. As well as the reduction of the unwanted amino alcohol, other by-products are also distinctly suppressed, for example bicyclic compounds and those by-products which result from the elimination of HCN.

Particular reference is made to the problem of elimination of HCN from gamma-keto nitriles, such as IPN, in the literature (U.S. Pat. No. 3,352,913). Firstly, it is noted that HCN elimination reduces the yield of IPDA (EP 042 119, DE 44 26 472).

Secondly, it is pointed out that HCN acts as a catalyst poison and leads to deactivation of the hydrogenation catalyst (EP 394 967 A1, page 2 line 34 ff, page 3 line 44 ff). It is therefore advisable to conduct the imination step in such a way that a minimum amount of HCN is eliminated.

According to EP 913 387, selectivity can also be enhanced in the preparation of IPDA by using quaternary ammonium bases. Correspondingly modified catalysts, specifically in the case of use of a solvent, have a much longer service life than alkali-modified catalysts.

In addition, processes for preparing isophoronediamine are known from CN 104230721A, EP 2649042A and WO 2012126869A.

Document DE 199 33 450.1 describes metal catalysts which, in the form of hollow spheres, have a low bulk density of 0.3 to 1.3 g/ml. In addition to the catalysts, the use thereof in hydrogenation reactions is also claimed.

A process for preparing isophoronediamine is known from WO 2002051791. Catalysts in the form of hollow spheres are used.

SUMMARY OF THE INVENTION

The underlying object was to find a process for preparing 3-aminomethyl-3,5,5-trimethylcyclohexylamine by hydrogenation of isophoronenitrile, wherein the yield and selectivity in the reductive amination of isophoronenitrile for preparation of isophoronediamine were to be improved.

The present invention relates to a process for preparing isophoronediamine, comprising:

A) subjecting isophoronenitrile directly in one stage to aminating hydrogenation to give isophoronediamine in the presence of ammonia, hydrogen, a hydrogenation catalyst and an optional additive, and in the presence or absence of an organic solvent;

or

B) converting isophoronenitrile to isophoronediamine in at least two or more than two stages, wherein isophoronenitrile is first converted fully or partly to isophoronenitrile imine, and the isophoronenitrile imine is subjected to aminating hydrogenation to give isophoronediamine as a pure substance or in a mixture with another component and/or isophoronenitrile, wherein the aminating hydrogenation proceeds in the presence of at least ammonia, hydrogen and a catalyst;

wherein the catalyst has, after catalyst activation, in its entirety, the following composition in percent by weight (% by weight), wherein the proportions add up to 100% by weight, based on the metals present:

cobalt: 55% to 95% by weight,
aluminum: 5% to 45% by weight,
chromium: 0% to 3% by weight, and
nickel: 0% to 7% by weight; and wherein the catalyst is in the form of hollow spheres having a diameter of 1 to 8 mm.

In another embodiment, the present invention relates to a catalyst for preparation of isophoronediamine, wherein the catalyst has, after catalyst activation, in its entirety, the following composition in percent by weight (% by weight), wherein the proportions add up to 100% by weight, based on the metals present:
cobalt: 55% to 95% by weight,
aluminum: 5% to 45% by weight,
chromium: 0% to 3% by weight, and
nickel: 0% to 7% by weight; and
wherein the catalyst is in the form of hollow spheres having a diameter of 1 to 8 mm.

BRIEF DESCRIPTION OF THE DRAWINGS

FIG. 1 shows the IPDA yield/GC-% based on hours of operation for a catalyst according to the invention and a comparative catalyst.

DETAILED DESCRIPTION OF THE INVENTION

The ranges below include all values and subvalues between the lower and higher limit of the range.

Surprisingly, a novel catalyst as described in detail below has been found. Additional unexpected effects found were a higher activity, which enables lower reaction temperatures, and a better long-term stability of the catalyst.

It has now been found that, surprisingly, the inventive catalyst, consisting of hollow spheres having particular diameters, produced from a metal alloy after activation by alkalis, achieves the object of the invention, and a higher activity and better long-term stability of the catalyst have additionally been found.

The invention provides a process for preparing isophoronediamine, characterized in that
A) isophoronenitrile is subjected directly in one stage to aminating hydrogenation to give isophoronediamine in the presence of ammonia, hydrogen, a hydrogenation catalyst and possibly further additions, and in the presence or absence of organic solvents;
or
B) isophoronenitrile is converted to isophoronediamine in at least two or more than two stages, where isophoronenitrile is first converted fully or partly to isophoronenitrile imine, and this isophoronenitrile imine is subjected to aminating hydrogenation to give isophoronediamine as a pure substance or in a mixture with other components and/or isophoronenitrile, in the presence of at least ammonia, hydrogen and a catalyst;
where the catalyst has the following properties:
I.
The catalyst has, after the activation, in its entirety, the following composition in percent by weight (% by weight), where the proportions add up to 100% by weight, based on the metals present:
cobalt: 55% to 95% by weight
aluminum: 5% to 45% by weight
chromium: 0% to 3% by weight
nickel: 0% to 7% by weight
and
II.
The catalyst is in the form of hollow spheres having diameters of 1 to 8 mm.

The catalyst material consists of a metal alloy, the metal alloy having been surface activated by bases. The layer thickness of the activated layer on the particle surface of the catalyst is preferably 50 to 1500 micrometers (μm). It may also be greater or smaller. Accordingly, the catalytically active composition of the catalyst is present on the surface. Alternatively, it is possible in the context of the invention to almost entirely or entirely leach out the entire catalyst particle.

The inventive catalyst, after the activation, is present as hollow spheres.

After the activation, the inventive catalyst material has, in its entirety, the following composition in percent by weight (% by weight), where the proportions add up to 100% by weight, based on the metals present:
1st Variant
cobalt: 55% to 95% by weight
aluminium: 5% to 45% by weight
chromium: 0% to 3% by weight
nickel: 0% to 7% by weight
and/or
2nd Variant
cobalt: 55% to 90% by weight
aluminium: 5% to 44.5% by weight
chromium: 0.5% to 5% by weight
and; or
3rd Variant
cobalt: 55% to 88% by weight
aluminium: 5% to 44.5% by weight
nickel: 0.5% to 7% by weight
and/or
4th Variant
cobalt: 55% to 85% by weight
aluminium: 5% to 43.5% by weight
chromium: 0.5% to 3% by weight
nickel: 1% to 7% by weight
and/or
5th Variant
cobalt: 57% to 84% by weight
aluminium: 10% to 40% by weight
chromium: 1% to 2% by weight
nickel: 2% to 4% by weight "Entirety" means that there is no distinction in the composition between the content of the metals on the surface and in the activated layer and in the core of the catalyst particles; instead, everything is added together and calculated.

The catalyst is in the form of hollow spheres.

In addition, the inventive hollow sphere catalyst, after the activation, has the following diameters:

In general, the catalyst, i.e. the hollow spheres, may have diameters of 1 to 8 millimeters (mm).

In a first preferred variant of the invention, the diameters of the catalyst, i.e. the hollow spheres, vary from 2.5 to 5.5 millimeters (mm).

In a second preferred variant of the invention, the diameters of the catalyst, i.e. the hollow spheres, vary from 3 to 8 millimeters (mm).

In a third preferred variant of the invention, the diameters of the catalyst, i.e. the hollow spheres, vary from 1 to 3 millimeters (mm).

The alloy powder used for the production of the inventive catalyst has a preferred grain size of 5 to 150 micrometers (μm). However, the grain size chosen may also be smaller or larger.

The determination of the particle sizes is described in DIN ISO 9276-1 (September 2004) and 9276-2 (February 2006) and 92764 (February 2006) and 9276-6 (January 2012). In addition, exact details of the definition of particle sizes, the distribution of particle sizes and the measurement of particle sizes can be found in HORIBA® Scientific, A GUIDEBOOK TO PARTICLE SIZE ANALYSIS, 2012, from HORIBA® Instruments, Inc, Irvine, USA.

According to the invention, the distribution of the particle sizes and the measurement of the particle sizes can be determined by laser methods (ISO 13320, 2012), light methods or imaging methods.

Suitable methods and descriptions of screen analysis are given in:

DIN 66165-1:1987-04 Particle size analysis; sieve analysis; general principles, and in DIN 66165-2:1987-04 Particle size analysis; sieve analysis; procedure.

Paul Schmidt, Rolf Körber, Matthias Coppers: Sieben und Siebniasehinen: Grundlagen und Anwendung [Screens and Screening Machines: Fundamentals and Application], Wiley-VCH Verlag, 2003, ISBN 9783527302079, Chapter 4.4: Analysesiebung [Analytical Screening].

Jörg Hoffmann: Handbuch der Messtechnik [Handbook of Measurement Technology], Hanser Verlag, 2007, ISBN 978-3-446-40750-3, Chapter 3.12.16.2.1.

After the activation, the inventive hollow sphere catalyst more preferably has, in its entirety, the following composition in percent by weight (% by weight), where the proportions add up to 100% by weight, based on the metals present (fourth preferred embodiment):

cobalt: 57% to 84% by weight
aluminium: 10% to 40% by weight
chromium: 1% to 2% by weight
nickel: 2% to 4% by weight
and with
diameters of the hollow sphere catalyst, i.e. the hollow spheres, having a statistical distribution between 2.5 and 5.5 millimeters (mm),
and/or
diameters of the hollow sphere catalyst, i.e. the hollow spheres, having a statistical distribution between 3.5 and 6.5 millimeters (mm),
and/or
diameters of the hollow sphere catalyst, i.e. the hollow spheres, having a statistical distribution between 1 and 3 millimeters (mm),
and/or
diameters of the hollow sphere catalyst, i.e. the hollow spheres, having a statistical distribution between 3 and 8 millimeters (mm),
where up to 10 percent of the particles may also be outside said range of said lower limit or upper limit, but up to 10 percent in each case may also be outside said range of said lower limit and upper limit.

The inventive catalyst may be formed from one or more layers. These layers may be formed either from the same or from different catalyst materials, i.e. alloy powders. Alloy powders may differ in terms of the composition of the metals and/or the particle size. The use of fine alloy powder results in a compact shell structure having low porosity and a high mechanical stability. Coarse alloy powder, in contrast, gives a porous structure of the hollow sphere shell. This leads to an increase in the active surface area of the inventive hollow spheres.

It is possible to influence the activity and/or selectivity of the inventive catalyst via the composition of the alloy powder.

In addition, it is possible that the hollow spherical catalyst has a bimodal or multimodal distribution in relation to the diameters of the hollow spheres. In the case of a bimodal distribution, hollow spheres having two different diameters are accordingly used, and in the case of a multimodal distribution hollow spheres having at least three different diameters. Preferably, the hollow spheres according to the first to third variants and/or hollow spheres according to the fourth variant are selected.

In addition, it is also possible that the catalyst is formed from one or more layers and/or these layers consist either of identical and/or different catalyst materials, i.e. alloy powders, and/or that the hollow spherical catalyst has a bimodal or multimodal distribution in relation to the diameters of the hollow spheres.

The advantage underlying this invention is achieved through the use of catalysts in the form of hollow spheres. The production of the catalysts employed in the process according to the invention can be conducted in accordance with the method described in DE 199 33 450.1. In this method, a mixture of an alloy powder composed of catalytically active metals comprising aluminium, a metal that can be leached out, an organic binder and optionally an inorganic binder, water and promoters on spheres consisting of a thermally decomposable material. It is possible with preference to use polystyrene foam beads. The application of the mixture comprising the metal alloy to the polymer beads can preferably be conducted in a fluidized bed. Organic binders used may preferably be 0% to 10% by weight of polyvinyl alcohol and/or 0% to 3% by weight of glycerol. The coated polymer foam beads are subsequently calcined above 300° C., preferably within a range between 450 and 1300° C., in order to thermally remove the polymer foam and sinter the metal. This gives the hollow spheres a stable shape. After the calcination, the hollow spherical catalysts are activated by treatment with basic solutions, preferably alkali metal or alkaline earth metal hydroxides in water, even more preferably aqueous sodium hydroxide solution. The catalysts thus obtained have bulk densities between 0.3 and 1.3 kg/l.

According to the invention, the catalysts employed in the process take the form of hollow spheres. Hollow spheres are typically easy to produce and have high fracture resistance.

The hollow spherical catalysts employed in accordance with the invention may contain a binder. The binder enables greater strength of the hollow catalyst spheres, which is necessary because of the hollow shape thereof. Preferably, powders of the metals which are also present as catalytically active constituents in the catalyst alloy are added as binders in the production of the hollow catalyst spheres. Alternatively, it is possible to add other binders, especially other metals as binders. Preference is given to using no binder. Hollow spherical cobalt catalysts have adequate strength even without added binder.

In the process of the invention, it is possible to use hollow spherical Raney catalysts doped with other metals. The dopant metals are often also referred to as promoters. The doping of Raney catalysts is described, for example, in documents U.S. Pat. No. 4,153,578, DE 21 01 856, DE 21 00 373 or DE 20 53 799. Preferred elements for doping are elements of groups 1A, 2A, 3B to 7B, 8, 1B, 2B and 3A of the Periodic Table, and also germanium, tin, lead, antimony and bismuth. Particular preference is given to manganese, iron, vanadium, tantalum, titanium, tungsten, molybdenum, rhenium and/or metals of the platinum group. The proportion of promoters and the catalyst may preferably be 0% to 5% by weight. The promoters may already be present as an alloy constituent, or only be added at a later juncture, especially after the activation.

During the production of the inventive catalyst, one or more calcinations are required at temperatures above 300° C., preferably within a range between 450 and 1300° C. If this operation is conducted under an oxygenous atmosphere, oxygen can be incorporated into the catalyst layer. The proportion in the catalyst is dependent on the duration of the calcination and/or the activation conditions and may preferably be 0% to 25% by weight.

If elements of this kind are present in an amount of not more than about 30% by weight, the proportion of the abovementioned Co and Al and any Cr and Ni metal in the catalyst is reduced correspondingly, in which case the proportions of Co and Al and any Cr and Ni add up to at least 70% by weight after the activation, based on the metals present.

In the process according to the invention, hollow spherical catalysts having a diameter of 1 to 8 mm and a shell thickness of 50 to 1500 micrometers (µm) are used. The catalyst shells may be impervious or have a porosity of 80% or higher.

In the process according to the invention, it is possible to use hollow spherical catalysts consisting of one or more layers. If the catalyst bodies have two or more layers, the catalyst bodies are dried between the individual coating steps in the course of production. This is preferably conducted in the fluidized bed at temperatures of 60 to 150° C. It is also possible to produce a hollow spherical catalyst having several layers, in which case there is no drying between the individual coating steps.

During the process according to the invention, the hollow spherical catalysts are used in the activated form. The metal that can be leached out which is present in the non-activated catalyst bodies may have been wholly or only partly leached out with alkalis in the activated state.

General method for production of the catalyst:

a) Production of the Alloy

The alloy is produced by thermal means, for example in an induction oven. This involves melting the metals to obtain an alloy. The finished melt is cast to bars, for example, for further processing.

b) Production of the Powders

The alloy is processed to powder in suitable equipment, for example precomminuted by means of a jaw crusher and ground further by means of a ball mill or nod mill. An optional screening step can give the desired size distribution of the particles through the choice of the appropriate screens.

c) Production of the Hollow Spheres

For the production of the hollow spheres, a mixture of alloy powder, an organic and optionally inorganic binder, water and promoters is applied to spheres consisting of a thermally decomposable material. It is possible with preference to use polystyrene foam beads. The application of the mixture containing the metal alloy to the polymer beads can preferably be conducted in a fluidized bed. Organic binders used may preferably be 0% to 10% by weight of polyvinyl alcohol and/or 0% to 3% by weight of glycerol. The coated polymer foam beads are subsequently calcined above 300° C., preferably within a range between 450 and 1300° C., in order to thermally remove the polymer foam and sinter the metal. This gives the hollow spheres a stable shape.

d) Activation of the Catalyst

The catalyst is activated in suitable apparatus. It is possible here to use organic or inorganic bases. Preference is given to using an alkali (e.g. sodium hydroxide solution), in which case an exothermic operation results in leaching of a portion of the aluminium out of the alloy with formation of hydrogen and alkali metal aluminate. The concentration of the alkali may be between 5% and 30% by weight, and the reaction temperature between 50 and 110° C. The degree of activation is determined via the temperature and the reaction time. The reaction time is variable and depends on the reaction conditions and the desired degree of activation. After the activation, the catalyst is washed with cold alkali to remove the aluminate, then with water and then stored under water.

Other compositions can be produced analogously in the production step a) through the appropriate choice of the amounts of metals.

Preferably, the catalyst is produced in the sequence described. Alternatively, the catalyst can be activated prior to the production of the hollow spheres.

It is possible to conduct the process according to the invention in one stage or in at least two or more than two stages.

If the process is conducted in one stage, isophoronenitrile is subjected to aminating hydrogenation directly in the presence of ammonia, hydrogen, a catalyst and possibly further additions, and in the presence or absence of organic solvents.

The expression "in at least two or in more than two stages" means that isophoronenitrile is first converted fully or partly in a separate reactor or reactor section to isophoronenitrile imine, and this isophoronenitrile imine is subjected to aminating hydrogenation as a pure substance or in a mixture with other components, for example unconverted isophoronenitrile, in the presence of at least ammonia and hydrogen and a catalyst.

A preferred embodiment of the process according to the invention for preparing IPDA is a two-stage process: In the first stage, at least some of the IPN used, in the presence or absence of an imination catalyst and/or of solvents, is converted by reaction with ammonia to isophoronenitrile imine. The conversion of IPN to IPNI after the imination should be greater than 80%, preferably greater than 90%, more preferably greater than 95%.

In the second stage, the first stage reaction product, as obtained or after a further treatment and/or addition of further ammonia, is subjected to aminating hydrogenation over hydrogenation catalysts in the presence of at least ammonia and hydrogen and in the presence or absence of an organic solvent at a temperature of 20 to 150° C., preferably 40 to 130° C., and a pressure of 0.3 to 50 MPa, preferably 5 to 30 MPa.

In a further preferred embodiment, the conversion of IPN to IPDA is effected in three separate reaction spaces, in the first reaction space, IPN is converted to isophoronenitrile imine with excess ammonia over imination catalysts at temperatures between 20 and 150° C. and pressures between 5 and 30 MPa. In the second reaction space, the reaction products formed are hydrogenated with hydrogen in the presence of excess ammonia over hydrogenation catalysts at temperatures between 20 and 130° C. and pressures of 5 to 30 MPa. In the third reaction space, the reaction products formed are hydrogenated over the catalysts for use in accordance with the invention at temperatures between 100 and 160° C. and pressures of 5 to 30 MPa.

In order to accelerate the establishment of equilibrium in the imination reaction, it is appropriate to use an imination catalyst. For this purpose, the imination catalysts known according to the related art can be used. Suitable catalysts are, for example, inorganic or organic ion exchangers (see EP 042 119), supported heteropolyacids (see DE 44 26 472), acidic metal oxides, especially aluminium oxide and titanium dioxide see EP 449 089), organopolysiloxanes containing sulpho groups (DE 196 27 265.3), and acidic zeolites and activated carbon (EP 061 137), in the case of use of an imination catalyst, the reaction temperature may be between 10 and 150° C., preferably between 30 and 130° C. and most preferably between 40 and 100° C. The pressure is between the autogenous pressure of the mixture and 50 MPa. Preference is given to conducting the imination reaction at the pressure at which the subsequent reductive amination is also conducted.

Even though the imination of isophoronenitrile with liquid ammonia is preferably conducted without addition of further solvents, it is also possible to work in the presence of additional solvents. Suitable solvents are monohydric alcohols having 1 to 4 carbon atoms, especially methanol, and ethers, particularly THF, MTBE and dioxane.

In the imination stage, between 1 and 500 mol, preferably 5 and 200 mol, more preferably between 5 and 100 mol, of ammonia are used per mole of IPN used. Typical catalyst hourly space velocities are in the range from 0.01 to 10 kg of IPN per kg of catalyst and hour, preferably 0.5 to 10 and more preferably 0.5 to 5 kg of IPN per kg of catalyst and hour.

In the case of imination in the presence of an imination catalyst, the catalyst may be present in the form of a suspension catalyst or fixed bed catalyst. It is advantageous to use fixed bed catalysts. In a particularly preferred embodiment, IPN and ammonia are passed continuously from the bottom upward through a reaction tube filled with imination catalyst.

The hydrogenation is effected in fixed bed reactors. Suitable reactor types are, for example, shaft furnaces, tray reactors or shell and tube reactors.

The hydrogenation is typically effected at temperatures between 20 and 150° C., preferably 40 and 130° C., and pressures of 0.3 to 50 MPa, preferably 5 to 30 MPa. It is also possible to perform the hydrogenation in the presence of the solvents already mentioned for the imination stage. The main advantage in the case of use of a solvent is that the hydrogenation can be conducted at lower pressures between 0.3 and 10 MPa.

The hydrogen required for the hydrogenation can be supplied to the reactor either in excess, for example at up to 10 000 molar equivalents, or only in such an amount that the hydrogen consumed by reaction and the portion of the hydrogen which leaves the reactor dissolved in the product stream is replenished. In the case of a continuous mode of operation, the hydrogen can be supplied in cocurrent or countercurrent.

In a preferred embodiment, the hydrogenation is effected in liquid ammonia as solvent. Between 1 and 500 mol, preferably 5 and 200 mol, more preferably between 5 and 100 mol, of ammonia are used per mole of IPN. It is appropriate to use at least the amount of ammonia which has been established in the upstream imination. However, the ammonia content can also be increased to the desired value before the hydrogenation by addition of additional ammonia.

The required volume of the hydrogenation catalysts to be used is guided by the LHSV (liquid hourly space velocity), which is dependent on the operating pressure, the temperature, the concentration and the catalyst activity and has to be observed in order to ensure maximum completeness of hydrogenation of the IPN used. Typically, the LHSV in the case of use of the mixture of IPN, ammonia and hydrogen, the use of which is preferred, is between 0.5 and 5 liters of IPN/ammonia mixture per liter of catalyst and hour, preferably between 1 and 4 $l_{sol} l_{cat}^{-1} h^{-1}$.

It is preferable that the hydrogenation catalysts for use are first conditioned with ammonia before they are used in the hydrogenation. For this purpose, the catalysts are contacted with ammonia or with mixtures of ammonia and one or more solvents. The conditioning preferably follows installation of the catalysts in the hydrogenation reactor, but it can also precede the installation of the catalysts. For conditioning, between 0.2 and 3, preferably 0.5 and 2, m³ of ammonia per m³ of catalyst and hour are used. It is customary to work at temperatures between 20 and 150° C., preferably 40 to 130° C. Particular preference is given to running through a temperature ramp in which the catalyst, beginning at moderately elevated temperature, preferably between 20 and 50° C., is heated gradually up to the reaction temperature desired at a later stage for the hydrogenation, preferably 20 to 150° C. The conditioning is preferably conducted in the presence of hydrogen, the partial pressure of the hydrogen used in the reactor covering the range from 0.1 to 50 MPa, preferably 5 to 40 MPa, more preferably 10 to 30 MPa. The duration of the conditioning, depending on the amount of ammonia used, is preferably between 1 and 48 h, more preferably between 12 and 24 h.

In the preferred two-stage process, the mixture comprising isophoronenitrile imine is hydrogenated in the presence of the hydrogenation catalyst in the second stage. The mixture supplied to the hydrogenation stage may directly be any which is obtained in the imination of IPN with ammonia in the first stage, or as obtained after addition or removal of components, for example ammonia, organic solvents, bases, cyanide salts, hydrocyanic acid and/or water. Preference is given to conducting the hydrogenation continuously in fixed bed reactors which can be operated in trickle mode or liquid phase mode. Suitable reactor types are, for example, shaft furnaces, tray reactors or shell and tube reactors. It is also possible to connect a plurality of fixed bed reactors in series for the hydrogenation, in which case each of the reactors is operated either in trickle bed mode or liquid phase mode.

Apart from the aforementioned constituents of the mixture to be supplied to the imination stage, this may additionally comprise higher- or lower-boiling fractions than IPDA from the distillative workup of the reaction mixture drawn off from the trickle bed reactor. Such fractions may, apart from residues of IPDA, also comprise those by-products from which IPDA forms again under reaction conditions. It is particularly advantageous to recycle the higher-boiling fraction than IPDA, which, apart from residues of IPDA, comprises 2-aza-4,6,6-trimethylbicyclo[3.2.1]octane as the main product. It is likewise particularly advantageous to recycle incompletely converted IPN, especially fractions comprising isophoroneaminonitrile. The recycled material can also, if desired, be added directly to the reaction mixture to be supplied to the hydrogenation stage.

In the hydrogenation of IPN or isophoronenitrile imine, it is possible to form two different stereoisomers. Through the choice of a temperature profile in the hydrogenation step, it is possible to influence the isomer ratio. It is possible, for example, first to partly hydrogenate a mixture comprising IPN or isophoronenitrile imine at a temperature between 20 and 90° C., and then to complete the reaction in a second step within a temperature range between 90 and 150° C. Through the observation of relatively low reaction temperatures in the 1st step, the selectivity can be shifted in favor of the cis isomer. The observation of relatively low reaction temperatures at the start of the reaction additionally has the advantage that the thermally labile isophoronenitrile imine is hydrogenated under particularly gentle conditions, and side reactions are suppressed as a result. Isophoroneaminonitrile, which is formed as an intermediate, is much more thermally stable and can therefore be hydrogenated at higher temperatures without any risk of further side reactions. The unwanted side reactions also include the elimination of HEN. In the process according to the invention, a certain cyanide ion concentration has a positive effect on the selectivity of the hydrogenation stage. This effect becomes increasingly apparent when the cyanide ions are present from the start in the hydrogenation stage and not just formed during the hydrogenation. Therefore, elimination of HCN during the hydrogenation stage should be avoided.

The desired temperature profile can be implemented, for example, by the series connection of two or more separately heatable reactors. It is also possible to implement a rising temperature profile in only one hydrogenation reactor. Particular preference is given to conducting the hydrogenation reaction in an adiabatically operated trickle bed reactor, in which the reaction mixture is supplied to the reactor at temperatures between 20 and 90° C., and owing to the heat of reaction which occurs and is absorbed by the reaction mixture leaves it again between 90 and 150° C.

The reaction mixture leaving the hydrogenation is purified further by the customary methods, in order to obtain an IPDA with the desired quality. It is possible here to use all standard separation methods, for example distillation, flash evaporation, crystallization, extraction, sorption, permeation, phase separation or combinations of the above. The purification can be conducted continuously, batchwise, in one or more stages, under reduced pressure or under pressure. Possible components which are removed, for example, in the farther purification are hydrogen, ammonia, water, and by-products obtained in the preparation of IPDA from IPN, for example hydrogenated HCN elimination products or impurities in the IPN, methylated by-products and/or incompletely hydrogenated intermediates.

Preferably, the purification is achieved by distillation under pressure and/or under reduced pressure in a plurality of steps. For this purpose, it is possible to use any desired distillation columns with or without internals, for example dephlegmators, dividing walls, unordered internals or random packings, ordered internals or structured packings, or trays with or without forced flow.

In a first step, especially hydrogen, inert gases, ammonia, low-boiling impurities and possibly also water are removed fully or partly in one or more distillation columns. The removal is preferably effected at a pressure lower than in the reaction step. If the removal is effected in a plurality of distillation steps, it is advantageous to lower the pressure stepwise. Most preferably, the removal is effected above 1 bar and with bottom temperatures of 0 to 200° C. The use of a stripping gas for removal of low-boiling impurities may be advantageous. Especially ammonia and hydrogen and proportions of the low-boiling impurities can be recycled fully or partly into the process (reaction). The tow-boiling impurities and possibly proportions of hydrogen and ammonia are sent to thermal utilization.

In a second step, further low-boiling impurities, water and high-boiling impurities are fully or partly removed. This can be effected in one or more distillation columns. This may involve distilling water off together with organic, low-boiling impurities and possibly proportions of IPDA via the top of the column and, after condensation, separating them into an aqueous phase and an organic phase. In this case, the organic phase can be recycled partly as reflux into the column. If the second step of the distillation is conducted in a single column (for example a dividing wall column), the IPDA is withdrawn via a sidestream with the desired purity, while the high-boiling impurities are obtained in the bottom of the column. If the separation, however, is conducted in two or more stages, the IPDA is obtained at the top of a column. The low- and high-boiling impurities and water are preferably removed under a reduced pressure between 100 Pa and 0.0999 MPa and bottom temperatures of 50 to 300° C. All secondary components can be sent to thermal utilization.

Having generally described this invention, a further understanding can be obtained by reference to certain specific examples which are provided herein for purposes of illustration only, and are not intended to be limiting unless otherwise specified.

EXAMPLES

Example A: Production of the Catalyst

Production of the Alloy

The alloy was produced in an induction oven. This involved melting the metals in the appropriate amounts at 1500° C. The finished melt was cast to bars for further processing.

Production of the Powders

The alloy bars were precomminuted by means of a jaw crusher and ground further by means of a ball mill. A screening step gave the desired size distribution of the granules through the choice of the appropriate screens.

Example 1: Production of the Hollow Spheres

By suspending 3179 g of CoAlCrNi alloy (particle size distribution<200 µm) in 2861 g of an aqueous solution having a content of about 2% by weight of polyvinyl alcohol, a coating solution was produced. The suspension was then sprayed on to 1500 ml of polystyrene spheres having a diameter around about 1.8 min while they were suspended in air stream directed upward.

1.5 l of these beads were further coated with a coating solution consisting of 3169 g of CoAlCrNi alloy suspended in 2852 g of an aqueous solution having a content of about 2% by weight of polyvinyl alcohol.

After the polystyrene beads had been coated with the aforementioned solutions, the beads were heated to 500° C., in order to burn out the polystyrene. The hollow CoAlCrNi beads were then heated to 900° C.

After cooling, the hollow beads were activated in a 20% by weight sodium hydroxide solution at 90° C. for 70 minutes. The activated hollow beads obtained have a diameter of 2.5 to 5.5 mm and a coat thickness of 600 to 1000 µm.

The catalyst used had, after the activation, in its entirety, the following composition in percent by weight (% by weight), where the proportions add up to 100% by weight, based on the metals present:
  cobalt: 55.6% by weight
  aluminium: 20.9% by weight
  chromium: 1.1% by weight
  nickel: 1.7% by weight
  oxygen: 20.8% by weight Example 2

The catalysts were tested for their catalytic efficacy in the preparation of 3-aminomethyl-3,5,5-trimethylcyclohexylamine (isophoronediamine, IPDA) from 3-cyano-3,5,5-trimethylcyclohexanone (isophoronenitrile, IPN) in a two-stage process.

In the first stage, isophoronenitrile was at least partly converted to 3-cyano-3,5,5-trimethylcyclohexane imine with ammonia in the presence of an imination catalyst and, in the second stage, subjected to aminating hydrogenation with hydrogen in the presence of ammonia over a hydrogenation catalyst at a temperature of 60 to 100° C. and a pressure of 250 bar. Each stage of the preparation was conducted in a separate reactor. However, the two reactors are connected in series and their temperatures were controlled individually.

The hydrogenation reactor was charged with 62 ml of the catalyst to be tested. The input solution of IPN (14% by weight) and ammonia (86% by weight) was pumped through the reaction tube from the top downward at a mass flow rate of 165 ml/h. The hydrogen was added separately, likewise from the top, at a volume flow rate of 40 l/h. The product liquid was collected in a collecting vessel beneath the reactor. The collected product mixture was analyzed by gas chromatography for IPDA and corresponding secondary components. The results are listed in Table 1.

TABLE 1

| Temperature | IPDA yield/GC % | Conversion/% |
| --- | --- | --- |
| 100° C. | 97.6 | 99.9 |
| 80° C. | 96.0 | 98.1 |
| 60° C. | 71.9 | 75.5 |

Long-Term Stability

In the first stage, isophoronenitrile was at least partly converted to 3-cyano-3,5,5-trimethylcyclohexane imine with ammonia in the presence of an imination catalyst and, in the second stage, subjected to aminating hydrogenation with hydrogen in the presence of ammonia over a hydrogenation catalyst at a temperature of 100° C. and a pressure of 250 bar. Each stage of the preparation was conducted in a separate reactor. However, the two reactors were connected in series and their temperatures were controlled individually.

For the testing of long-term stability, the hydrogenation reactor was charged with 6 l of the catalyst to be tested. The input solution of IPN (24% by weight) and ammonia (76% by weight) was pumped through the reaction tube from the top downward at a volume flow rate of 10 l/h. In addition, hydrogen was added, likewise from the top. The product liquid was collected in a collecting vessel beneath the reactor. The collected product mixture was analyzed by gas chromatography for IPDA and corresponding secondary components. The results are shown in FIG. 1.

Inventive catalyst: hollow cobalt spheres of the composition as described above in Example 1.

Reference catalyst: supported compressed shaped cobalt catalyst bodies.

European patent application EP15161579 filed Mar. 30, 2015, is incorporated herein by reference.

Numerous modifications and variations on the present invention are possible in light of the above teachings. It is therefore to be understood that within the scope of the appended claims, the invention may be practiced otherwise than as specifically described herein.

The invention claimed is:

1. A process for preparing isophoronediamine, comprising:
   A) subjecting isophoronenitrile directly in one stage to aminating hydrogenation to give isophoronediamine in the presence of ammonia, hydrogen, a catalyst and an optional additive, and in the presence or absence of an organic solvent;
   or
   B) converting isophoronenitrile to isophoronediamine in at least two or more than two stages,
   wherein isophoronenitrile is first converted fully or partly to isophoronenitrile imine, and the isophoronenitrile imine is subjected to aminating hydrogenation to give isophoronediamine as a pure substance or in a mixture with another component and/or isophoronenitrile,
   wherein the aminating hydrogenation proceeds in the presence of at least ammonia, hydrogen and a catalyst;
   wherein the catalyst has, after catalyst activation, in its entirety, the following composition in percent by weight (% by weight), wherein the proportions add up to 100% by weight, based on the metals present:
   cobalt: 55% to 85% by weight,
   aluminium: 5% to 43.5% by weight,
   chromium: 0.5% to 3% by weight, and
   nickel: 1% to 7% by weight; and
   wherein the catalyst is in the form of hollow spheres having a diameter of 1 to 8 mm.

2. The process for preparing isophoronediamine according to claim 1, wherein the catalyst has, after catalyst activation, in its entirety, the following composition in percent by weight (% by weight), wherein the proportions add up to 100% by weight, based on the metals present:
   cobalt: 57% to 84% by weight,
   aluminium: 10% to 40% by weight,
   chromium: 1% to 2% by weight, and
   nickel: 2% to 4% by weight.

3. The process for preparing isophoronediamine according to claim 1, wherein the diameter of the catalyst hollow spheres ranges from 2.5 to 5.5 millimeters (mm),
   and/or
   the diameter of the catalyst hollow spheres ranges from 3 to 8 millimeters (mm),
   and/or
   the diameter of the catalyst hollow spheres ranges from 1 to 3 millimeters (mm).

4. The process for preparing isophoronediamine according to claim 1, wherein the catalyst has, after catalyst activation, in its entirety, the following composition in percent by weight (% by weight), wherein the proportions add up to 100% by weight, based on the metals present:
   cobalt: 57% to 84% by weight,
   aluminium: 10% to 40% by weight,
   chromium: 1% to 2% by weight, and
   nickel: 2% to 4% by weight; and
   wherein the diameters of the catalyst hollow spheres have a statistical distribution between 2.5 and 5.5 millimeters (mm),
   and/or
   wherein the diameters of the catalyst hollow spheres have a statistical distribution between 3.5 and 6.5 millimeters (mm),
   and/or
   wherein the diameters of the catalyst hollow spheres have a statistical distribution between 1 and 3 millimeters (mm),
   and/or
   wherein the diameters of the catalyst hollow spheres have a statistical distribution between 3 and 8 millimeters (mm), and
   wherein up to 10 percent of the catalyst hollow spheres are optionally outside said range of said lower limit or upper limit of said statistical distribution, but up to 10 percent in each case are optionally outside said range of said lower limit and upper limit of said statistical distribution.

5. The process for preparing isophoronediamine according to claim 1, wherein the catalyst further comprises at least one doping metal selected from the group consisting of manganese, iron, vanadium, tantalum, titanium, tungsten, molybdenum, rhenium, metals of the platinum group and mixtures thereof.

6. The process for preparing isophoronediamine according to claim 5, wherein the proportion of dopant metal in the catalyst is 0% to 5% by weight.

7. The process for preparing isophoronediamine according to claim 1, wherein the proportion of oxygen in the catalyst is 0% to 25% by weight.

8. The process for preparing isophoronediamine according to claim 1, wherein the catalyst comprises one or more layers and/or the layers comprise the same and/or a different catalyst material, and/or wherein the hollow sphere catalyst has a bimodal or multimodal distribution in relation to the diameters of the hollow spheres.

9. The process for preparing isophoronediamine according to claim 1, wherein at least some of the isophoronenitrile (IPN) used is converted, in the first stage by reaction with ammonia in the presence or absence of an imination catalyst and/or of a solvent, to isophoronenitrile imine (IPNI), and the conversion of IPN to IPNI after the imination being greater than 80%.

10. The process for preparing isophoronediamine according to claim 1, wherein the first stage reaction product, as obtained or after a further treatment and/or addition of further ammonia, is subjected in the second stage to aminating hydrogenation over hydrogenation catalysts in the presence of at least ammonia and hydrogen and in the presence or absence of an organic solvent at a temperature of 20 to 150° C. and a pressure of 0.3 to 50 MPa.

11. The process for preparing isophoronediamine according to claim 1, wherein the conversion of isophoronenitrile to isophoronediamine is effected in three separate reaction spaces, IPN being converted to isophoronenitrile imine with excess ammonia over imination catalysts in the first reaction space at temperatures between 20 and 150° C. and pressures between 5 and 30 MPa, the reaction products formed being hydrogenated with hydrogen in the presence of excess ammonia over hydrogenation catalysts in the second reaction space at temperatures between 20 and 130° C. and pressures of 5 to 30 MPa, and the reaction products formed being hydrogenated over catalysts in the third reaction space at temperatures between 100 and 160° C. and pressures of 5 to 30 MPa.

12. The process for preparing isophoronediamine according to claim 1, wherein the imination reaction is effected in the presence of at least one imination catalyst.

13. The process for preparing isophoronediamine according to claim 1, wherein the imination of isophoronenitrile with liquid ammonia is conducted without addition of further solvent.

14. The process for preparing isophoronediamine according to claim 1, wherein between 1 and 500 mol of ammonia is used per mole of isophoronenitrile used in the imination stage.

15. The process for preparing isophoronediamine according to claim 1, wherein the imination is conducted in the presence of a suspension catalyst or fixed bed catalyst.

16. The process for preparing isophoronediamine according to claim 1, wherein isophoronenitrile and ammonia in the imination are conducted continuously from the bottom upward through a reaction tube filled with imination catalyst.

17. The process for preparing isophoronediamine according to claim 1, wherein the hydrogen required for the hydrogenation is supplied to the reactor either in excess or in such an amount that the hydrogen consumed by reaction and the portion of the hydrogen which leaves the reactor dissolved in the product stream is replenished.

18. The process for preparing isophoronediamine according to claim 1, wherein the hydrogenation is conducted in liquid ammonia as solvent, using between 1 and 500 mol of isophoronenitrile.

19. The process for preparing isophoronediamine according to claim 1, wherein the catalyst is first conditioned with ammonia before it is used in the hydrogenation.

20. The process for preparing isophoronediamine according to claim 1, wherein the hydrogenation is effected continuously in a fixed bed reactor.

21. The process for preparing isophoronediamine according to claim 1, wherein the hydrogenation is conducted continuously in a fixed bed reactor which is operated in trickle mode or liquid phase mode.

22. The process for preparing isophoronediamine according to claim 1, wherein the reaction mixture leaving the hydrogenation is purified in one or more stages, and the isophoronediamine is obtained.

23. The process for preparing isophoronediamine according to claim 1, wherein the reaction mixture leaving the hydrogenation is purified in two steps, with complete or partial removal of hydrogen, an inert gas, ammonia, a low-boiling impurity and optionally water in one or more distillation columns in a first step, and complete or partial removal of further low-boiling impurities, water and high-boiling impurities in distillation columns in a second step, and the isophoronediamine is obtained.

* * * * *